(12) United States Patent
Hong et al.

(10) Patent No.: US 7,989,666 B2
(45) Date of Patent: Aug. 2, 2011

(54) METHOD FOR PREPARING BISPHENOL A

(75) Inventors: Dongyi Hong, Beijing (CN); Jidong Zhou, Beijing (CN); Jinlai Qin, Beijing (CN); Xuelei Li, Beijing (CN); Zhenwei Yao, Beijing (CN); Hongjiang Zhang, Beijing (CN); Cuiyun Liu, Beijing (CN); Weihua Fan, Beijing (CN)

(73) Assignee: China Petroleum & Chemical Corporation, Beijing (CN)

( * ) Notice: Subject to any disclaimer, the term of this patent is extended or adjusted under 35 U.S.C. 154(b) by 344 days.

(21) Appl. No.: 10/573,697

(22) PCT Filed: Sep. 24, 2004

(86) PCT No.: PCT/CN2004/001097
§ 371 (c)(1),
(2), (4) Date: Mar. 13, 2007

(87) PCT Pub. No.: WO2005/030687
PCT Pub. Date: Apr. 7, 2005

(65) Prior Publication Data
US 2008/0091051 A1    Apr. 17, 2008

(30) Foreign Application Priority Data
Sep. 28, 2003    (CN) .................................. 03 1 60098

(51) Int. Cl.
*C07C 39/16*    (2006.01)
(52) U.S. Cl. ......... 568/728; 568/722; 568/727; 568/749
(58) Field of Classification Search .................. 568/728, 568/722, 727, 749
See application file for complete search history.

(56) References Cited

U.S. PATENT DOCUMENTS

| 2,486,342 | A | * | 10/1949 | Taylor et al. ..................... 203/18 |
| 4,308,404 | A | * | 12/1981 | Kwantes et al. ............... 568/727 |

(Continued)

FOREIGN PATENT DOCUMENTS

CA    706434    3/1965

(Continued)

OTHER PUBLICATIONS

Japanese Office Action of Feb. 14, 2011 and English Translation.

*Primary Examiner* — Jafar Parsa
*Assistant Examiner* — Yate K Cutliff
(74) *Attorney, Agent, or Firm* — Ladas & Parry LLP

(57) ABSTRACT

The present invention discloses a method for preparing bisphenol A, comprising the following steps: transferring phenol and acetone into a reaction zone charged with condensation catalyst, obtaining a stream containing bisphenol A after reaction; transferring the obtained stream containing bisphenol A into a rectification zone, obtaining a product fraction primarily containing bisphenol A and phenol; and transferring the product fraction primarily containing bisphenol A and phenol into a crystallization zone to obtain a bisphenol A product; wherein a water-depleted fraction primarily containing phenol, bisphenol A and acetone is obtained from the rectification zone, and said water-depleted fraction is cooled and returned as a cycled stream to the reaction zone. Through cycling the water-depleted fraction to the reaction zone, the water content within the reaction zone can be reduced, the catalytic activity can be maintained and the reaction temperature rise can be controlled, thus the conversion of acetone and the selectivity of reaction can be improved accordingly.

12 Claims, 1 Drawing Sheet

U.S. PATENT DOCUMENTS

| | | | |
|---|---|---|---|
| 5,087,767 A * | 2/1992 | Okamoto et al. | 568/727 |
| 5,648,561 A * | 7/1997 | Tan et al. | 568/727 |
| 6,277,945 B1 * | 8/2001 | Hachiya et al. | 528/196 |

FOREIGN PATENT DOCUMENTS

| | | | |
|---|---|---|---|
| CN | 1118155 | | 3/1996 |
| EP | 0812815 A1 | | 12/1998 |
| EP | 1006143 | | 6/2000 |
| EP | 1346973 | | 9/2003 |
| GB | 1578952 | | 5/1978 |
| JP | 41-4454 | | 8/1961 |
| JP | 54-019951 | * | 2/1979 |
| JP | 54-19952 | | 2/1979 |
| JP | 10-59888 | | 3/1998 |
| JP | 2000-159925 | | 6/2000 |
| JP | 2002-69023 | | 3/2002 |
| JP | 2002-193862 | | 10/2002 |
| JP | 2003-80002 | | 3/2003 |

* cited by examiner

METHOD FOR PREPARING BISPHENOL A

TECHNICAL FIELD

The present invention relates to a method for preparing bisphenol A, in particular to a method for preparing bisphenol A by continuous dehydration-condensation of phenol and acetone.

BACKGROUND ART

Bisphenol A has a chemical name of 2,2-di(4-hydroxyphenyl)propane, and is widely used as raw materials in industry, for example, it can be used to produce epoxy resin and polycarbonate, etc.

Bisphenol A can be synthesized by dehydration-condensation of excessive phenol and acetone in the presence of an acidic catalyst, and the specific reaction formula is as follows.

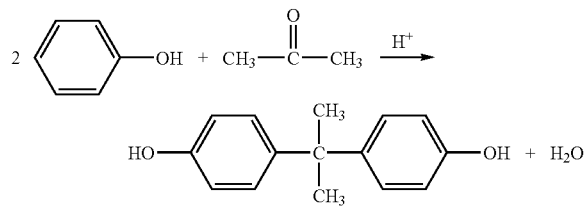

This reaction is an exothermic reaction. In an adiabatic fixed bed reactor, if there is no effective heat-removing means, the temperature in the reactor may rise significantly, while the current cation exchange resin as condensation catalyst may be inactivated under high temperature and side reactions may be enhanced at the same time. Thus, a plurality of cooling streams would be needed to prevent the temperature rise within an adiabatic fixed bed reactor.

For example, Chinese patent application CN1390819A discloses a method for producing bisphenol A, wherein the dehydration-condensation is conducted in an adiabatic fixed bed reactor, and two catalyst beds are provided in the reactor, wherein a portion of reaction mixture as cycled stream is received between said two catalyst beds, mixed with a feed stream to the reactor, and transferred into the upper portion of the reactor. The residual portion of the reaction mixture is discharged from the reactor and transferred into a distillation system, where the fraction of acetone-water-phenol is distilled out, and the resultant residue is crude bisphenol A, which is melted and crystallized progressively to obtain bisphenol A product. The drawback of this method is that the cycled stream is not dewarted, thus the water content in the reaction stream is high and adverse to the reaction obviously.

CN1406218A discloses a method for producing bisphenol A, which comprises charging phenol and acetone into a multistage reactor, wherein at least two adiabatic fixed bed reactors charged with cation exchange resin are arranged in series, a heat exchanger is provided at the inlet of each reactor in order to control the temperature within each reactor at a level of not greater than 90° C. However, this patent application merely points out that a heat exchanger is provided at the inlet of each reactor in order to control the reaction temperature, and no specific controlling means is mentioned in its specification and examples.

At present, cation exchange resin is the most widely used condensation catalyst; the resultant reaction stream is concentrated to remove the generated water, unreacted acetone and part of phenol; and then the concentrated reaction stream is transferred into post-treatment procedures such as crystallization, etc. to obtain bisphenol A product finally, wherein the unreacted phenol and acetone may be recovered and cycled back to the reaction system.

Qi xiwang and Chen Hongfang reported (Petrochemical Industry, 1996, 25(9):620-624): water is a strong poison for sulfonic acid type acidic ion exchange resin catalyst, and this may be explained as that a relatively firm hydrogen bond network may be formed between the water generated in the reaction and the sulfonic acid groups on the catalyst's framework and said network occupies the active catalytic sites, thus may inhibit the catalytic activity significantly. Thus, the lower the water content in the reaction stream, the more favored the reaction. In addition, water is one of reaction products, so its removal may promote the reaction forwardly.

Therefore, many studies have been conducted on how to remove the water generated in the reaction.

CN1118155A, CN1077187A and CN1080914A all mention that a condensation is conducted in a multistage suspended bed reaction column, and a stream of inert gas is fed at the bottom of the reactor to remove the water generated in reaction by gas stripping. Then, without concentration, the reaction stream is directly crystallized to form an adduct crystal of bisphenol A and phenol and a liquor. After solid-liquid separation, bisphenol A is obtained by removing phenol from the adduct crystal. However, the drawbacks of these methods lie in that the multistage suspended bed reactor has a complex structure and is difficult to construct, and many other devices may be needed to treat and cycle the inert gas at the same time.

U.S. Pat. No. 5,087,767 discloses a method for preparing bisphenol A, wherein part of the water generated in reaction is removed through a pervaporation from the reaction mixture containing phenol and acetone, wherein said pervaporation is performed by a selective water-permeable membrane, such as porous glass membranes, porous silica membranes, porous alumina membranes and porous ceramics membranes. According to said method, the water generated in reaction may be quickly removed by pervaporation simultaneously or alternatively as the reaction occurs so that high conversions of acetone and phenol and a high yield of bisphenol A are achieved. However, its drawback is that the capacity of separating water is limited. In addition, this method is merely suitable for a batchwise stirred reactor rather than a continuous fixed bed reactor.

SUMMARY OF THE INVENTION

An object of the present invention is to provide a method for preparing bisphenol A. By the method of the present invention, a water-depleted fraction can be withdrawn from a rectification zone in the process and can be cycled back to the reactor. Thus, on the one hand, the cycled water-depleted fraction can be used as cooling stream to control the reaction temperature; and on the other hand, the water content in the reactor can be reduced.

For said object, the present invention provides a method for preparing bisphenol A, comprising the following steps: transferring phenol and acetone into a reaction zone charged with condensation catalyst to obtain a stream containing bisphenol A after the reaction; transferring the obtained stream containing bisphenol A into a rectification zone to obtain a product fraction primarily containing bisphenol A and phenol; and transferring the product fraction primarily containing bisphenol A and phenol into a crystallization zone to obtain a bisphenol A product; wherein a water-depleted fraction primarily containing phenol, bisphenol A and acetone is obtained from the rectification zone and is returned to the reaction zone as a cycled stream after being cooled.

According to the method of the present invention, the water content in the cycled water-depleted fraction primarily containing phenol, bisphenol A and acetone is controlled at a level of not greater than 2% by weight, and said water-depleted fraction can be cooled by cooling water, or by heat-exchange with other streams, or by a combination thereof.

According to the method of the present invention, said reaction zone is one adiabatic fixed bed reactor, or comprises two or more adiabatic fixed bed reactors arranged in series. When said reaction zone comprises two or more adiabatic fixed bed reactors arranged in series, the water-depleted fraction primarily containing phenol, bisphenol A and acetone, which is withdrawn from the rectification zone, can be returned to any one of the reactors, or to each reactor proportionally, but preferably to the last reactor only the reason is that the concentration of bisphenol A in said water-depleted fraction is high and a backmixing may occur if said water-depleted fraction is returned to other reactors; at the same time, a heat exchanger is provided at the inlets of other reactors to control the condensation temperature therein, and the stream from reaction may pass through an adsorption column to remove harmful impurities as desired practically.

According to the method of the present invention, the weight ratio of the cycled flow rate of said water-depleted fraction primarily containing phenol, bisphenol A and acetone to the flow rate of the feed stream to the reactor into which said water-depleted fraction enters is in the range from 5:1 to 15:1, wherein the flow rate of the feed stream excludes the cycled flow rate. Since said cycled water-depleted fraction functions mainly to remove the reaction heat generated within the reactor, if the cycled flow rate is too little, the reaction heat can not be effectively removed, and a temperature rise will occur therein, so the catalytic activity will be influenced. Said water-depleted fraction primarily containing phenol, bisphenol A and acetone is preferably withdrawn in liquid.

According to the method of the present invention, when said reaction zone comprises two or more adiabatic fixed bed reactors arranged in series, phenol is fed into the first reactor once, and acetone is fed into the first reactor once, or into each reactor proportionally, preferably the acetone is fed into each reactor proportionally in order to enhance the relative concentration of phenol in each reactor and at the same time reduce the ratio of total phenol to total acetone to a level as low as possible.

Any solid catalyst suitable for the condensation between phenol and acetone and insoluble in the reaction mixture in the prior art can be used in the present invention. As for the continuous method of the present invention, it is preferable that the condensation catalyst is cation exchange resins, which can be unmodified, such as sulfonated styrene-divinyl-benzene copolymer, cross-linked sulfonated styrene polymer, etc., or modified, such as mercapto-modified cation exchange resin, etc. According to the method of the present invention, a cocatalyst can be used to accelerate the reaction, inhibit the by-products and improve the selectivity of reaction. Said cocatalyst can be alkylmercaptan, such as methylmercaptan, ethylmercaptan and thioglycollic acid, etc.

According to the method of the present invention, the condensation temperature in said reaction zone is in the range of 45-160° C., preferably 50-130° C., more preferably 60-100° C. According to the method of the present invention, if the temperature is lower than 45° C., the reaction may be too slow and a large charge of catalyst may be required; while if the reaction temperature is higher than 160° C., the catalyst may be inactivated readily, more by-products may be generated, and the selectivity of bisphenol A may decrease accordingly.

According to the method of the present invention, the pressure in said reaction zone is atmosphere or a positive pressure, generally from atmosphere to 6 kg/cm$^2$ (gage pressure, which represents a pressure measured on the basis of atmosphere).

According to the method of the present invention, the molar ratio of phenol to acetone in said reaction zone is generally in the range from 3:1 to 30:1, preferably from 5:1 to 15:1, because if said molar ratio is higher than 30:1, the reaction may be too slow, while if said molar ratio is lower than 3:1, more by-products may be generated, and the selectivity of bisphenol A may decrease accordingly.

According to the method of the present invention, said rectification zone can be a rectification column with side draws, a combination of a flash drum and a rectification column, or other devices capable of removing lights and water.

In the first embodiment according to the method of the present invention, said rectification zone can be one rectification column, wherein a water-depleted fraction primarily containing phenol, bisphenol A and acetone is withdrawn via a side draw, and said water-depleted fraction is cooled, mixed with feed streams and returned to the reaction zone; a product fraction primarily containing bisphenol A and phenol is discharged from the bottom of said rectification column, and transferred into a crystallization zone to obtain a bisphenol A product through further separation; while a fraction primarily containing water, acetone and phenol is discharged from the top of said rectification column, and further separated to recover acetone and phenol, and the recovered acetone and phenol is cycled back to the reaction zone.

According to said first embodiment, said rectification column can be a vacuum column or an atmospheric column, and its operation pressure is in the range of 50-800 mmHg (absolute pressure, which represents a pressure measured on the basis of absolute vacuum).

According to said first embodiment, the number of theoretical trays of said rectification column is generally in the range from 4 to 20. When said number is less than 4, lights can hardly be removed. Although the more the number, the more effective the separation, the cost of equipment increases significantly if the number is too large. Thus, with a comprehensive consideration, the number of theoretical trays of said rectification column is generally in the range from 4 to 20.

According to said first embodiment, said rectification column can be a plate column or a packed column, and the locations of the feeds and side draws of the column should be determined so that the water content in the water-depleted fraction primarily containing phenol, bisphenol A and acetone, which is withdrawn via a side draw, is not greater than 2% by weight.

According to said first embodiment, when said rectification column is a plate column, said feeding site can be at 0-3/5 of the total theoretical trays (counting from the top of the column), and the side draw can be at 1/5 to 4/5 of the stripping section (counting from the feeding site of the column). Thus, part of phenol, most acetone and water can be discharged from the top of the column, while the concentrated stream primarily containing bisphenol A and phenol is discharged from the bottom of the column, and a water-depleted fraction with a very low water content is withdrawn via a side draw at the same time.

According to said first embodiment, when said rectification column is a packed column, there are at least two packed sections below the feeding site, 0 to 1 packed section above the feeding site, and the side draw is located between the first packed section and the second packed section below and adjacent to the feeding site. If the column is packed above the feeding site, said packing is equivalent to 1-6 theoretical trays. The first packed section below and adjacent to the feeding site is equivalent to 2-6 theoretical trays.

The sum of other packed sections below and adjacent to the feeding site except for the first packed section is equivalent to 2-8 theoretical trays. Thus, part of phenol, most acetone and water can be discharged from the top of the column, while the concentrated stream primarily containing bisphenol A and phenol is discharged from the bottom of the column, and a water-depleted fraction with a very low water content is withdrawn via a side draw at the same time. The packings to be used can be common random packings or structured packings.

According to said first embodiment, for further concentrating the bottom stream, said rectification column is equipped with a heat exchanger at its lower portion, and said heat exchanger connects the lower portion of the column and its bottom outlet via pipelines to form a bottom reboiling system so that the water content in the side draw fraction can be further reduced at the same time as the bottom stream of the column is concentrated; said rectification column may also be equipped with a heat exchanger at its upper portion, said heat exchanger connects the upper portion of the column and its top outlet via pipelines to form a top refluxing system, so facilitate the effective separation within the column.

The top fraction of said rectification column primarily contains acetone, phenol and water, and any method suitable for separating phenol, acetone and water in the prior art can be used in the present invention. For example, the methods disclosed in U.S. Pat. No. 3,049,569, CN1390187A, CN1300729A, CN1118155A, etc. can be used to separate acetone, phenol and water, and the separated acetone and phenol can be cycled back to the reaction zone.

The bottom fraction of said rectification column primarily contains phenol and bisphenol A. According to the method of the present invention, the product fraction primarily containing bisphenol A and phenol is transferred into the crystallization zone for crystallization and separation to obtain a final bisphenol A product, wherein in said crystallization zone the crystallization can be carried out once only; and any method suitable for separating phenol and bisphenol A in the prior art can be used in the present invention. For example, the methods disclosed in U.S. Pat. No. 3,049,569, CN1390187A, CN1300729A, CN1118155A, etc. can be used to separate phenol and bisphenol A, and the separated phenol can be cycled back to the reaction zone, while the bisphenol A product can be used in industrial processes to produce epoxy resin and polycarbonate etc.

In another embodiment according to the method of the present invention, said rectification zone is a combination of a flash drum and a rectification column. In this case, the bisphenol A-containing stream from the reaction zone is transferred into the flash drum. A water-depleted fraction primarily containing phenol, bisphenol A and acetone is discharged from the bottom of the flash drum. Part of said water-depleted fraction is cycled back to the reaction zone, and the residual part is transferred into the rectification column. A fraction primarily containing phenol, a little amount of acetone and water is discharged from the top of said rectification column and can be further separated to recover phenol and acetone respectively, and a product fraction primarily containing bisphenol A and phenol is discharged from the bottom of said rectification column and is transferred into crystallization zone to obtain a bisphenol A product through further separation, while a fraction primarily containing water, acetone and phenol is discharged from the top of the flash drum and may also be separated to recover acetone and phenol, and the recovered acetone and phenol may also be cycled back to the reaction zone.

According to said another embodiment, the operation pressure of the flash drum in said rectification zone is in the range of 50-800 mgHg (absolute pressure), and column internals, equivalent to 0-2 theoretical trays, such as packings and trays are equipped in said flash drum, wherein said packings may also be common random packings or structured packings, and the flash drum to be used may also be equipped with internals such as trays, gauze, etc. to facilitate gas-liquid separation, and said flash drum can be replaced by other devices with flash capability.

According to said another embodiment, the reaction stream from the reaction zone is heated and then transferred into the flash drum in the rectification zone. When the pressure in the flash drum is stabilized, the temperature of the stream thereinto affects the water content of the fraction discharged from the bottom of the flash drum. Thus, the temperature of the stream entering into the flash drum should be determined so that the water content in the fraction discharged from the bottom of the flash drum is not greater than 2% by weight.

According to said another embodiment, part of the water-depleted fraction primarily containing phenol, bisphenol and acetone, which is discharged from the bottom of the flash drum, is transferred into the rectification column, wherein the operation pressure and the number of theoretical trays of said rectification column should be determined so that the bisphenol A concentration in the bottom product fraction is of 20-40% by weight in order to facilitate the subsequent crystallization and separation.

According to said another embodiment, as for the fraction discharged from the top of the flash drum and primarily containing acetone, phenol and water, and any method suitable for separating phenol, acetone and water in the prior art can be used to further treat this fraction. For example, the methods disclosed in U.S. Pat. No. 3,049,569, CN1390187A, CN1300729A, CN1118155A, etc. can be used to separate acetone, phenol and water, and the separated acetone and phenol can be cycled back to the reaction zone.

According to the method of the present invention, the product fraction primarily containing bisphenol A and phenol is transferred into the crystallization zone for further crystallization and separation to obtain a final bisphenol A product, wherein in said crystallization zone the crystallization can be carried out once only; and any crystallization method suitable for separating phenol and bisphenol A in the prior art can be used. For example, the methods disclosed in U.S. Pat. No. 3,049,569, CN1390187A, CN1300729A, CN1118155A, etc. can be used to separate phenol and bisphenol A, and the separated phenol can be cycled back to the reaction zone, while the bisphenol A product can be used in industrial processes to produce epoxy resin and polycarbonate etc.

In the method of the present invention, bisphenol A is prepared continuously by combining rectification zone and fixed bed reactor so that the catalytic activity can be maintained, and the conversion of acetone and the selectivity of reaction can be improved. According to the present invention, compared with the processes for continuously preparing bisphenol A by fixed bed reactor in the prior art, without addition of any device, water and lights can be removed by the same rectification column and the reaction product can be concentrated, and at the same time the water-depleted fraction with a very low water content, which is withdrawn via a side draw, can be cycled back to the reactor so that the operation can be very simple and the energy consumption can be reduced accordingly. In addition, according to the present invention, the processes for continuously preparing bisphenol A by fixed bed reactor in the prior art can be reschemed accordingly. For example, a flash drum can be provided upstream the original rectification column, and a water-depleted fraction with a very low water content discharged from the flash drum can be cycled back to the reactor, and the original rectification column can be used to further concentrate the reaction product.

BEST EMBODIMENTS OF THE PRESENT INVENTION

The present invention is further illustrated by the following examples with reference to the drawings, however, the present invention should not be restricted to these examples anyway.

Figure 1:
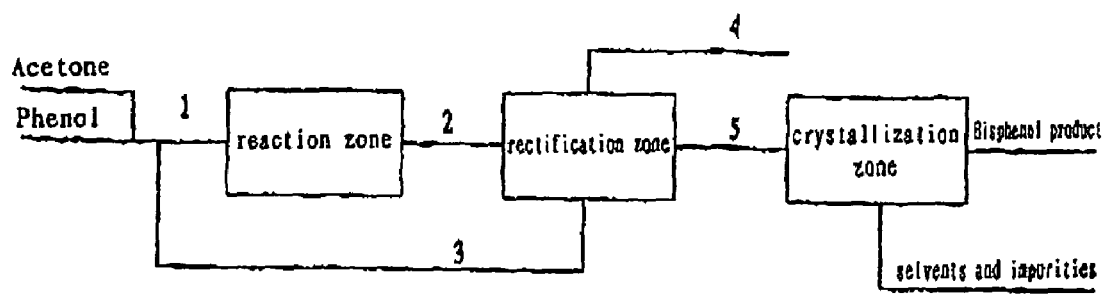
FIG. 1 is a schematic process flow diagram of the method according to the present invention for preparing bisphenol A.

The present invention provides a method for preparing bisphenol A (cf. FIG. 1), comprising the following steps: transferring a reaction stream 1, obtained by mixing phenol, acetone and a cycled stream, into a reaction zone charged with condensation catalyst, obtaining a stream 2 containing bisphenol A after the reaction; transferring the stream 2 into a rectification zone, cooling and returning the resultant water-depleted fraction 3 primarily containing phenol, bisphenol A and acetone as a cycled stream to the reaction zone; also obtaining a fraction 4 comprising water, unreacted acetone and part of unreacted phenol, and transferring said fraction 4 into a recovery process; in addition, obtaining a product fraction 5 primarily containing bisphenol A and phenol, further separating solvents and impurities from said product fraction 5 in a crystallization zone to finally obtain a bisphenol A product.

Figure 2:
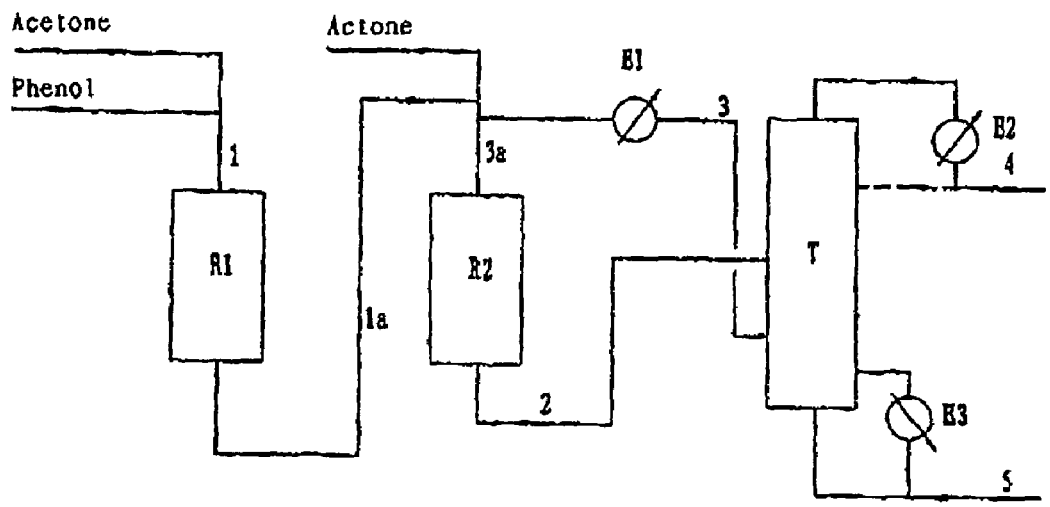
FIG. 2 is a schematic process flow diagram of the first embodiment of the method according to the present invention for preparing bisphenol A.
Figure 3:
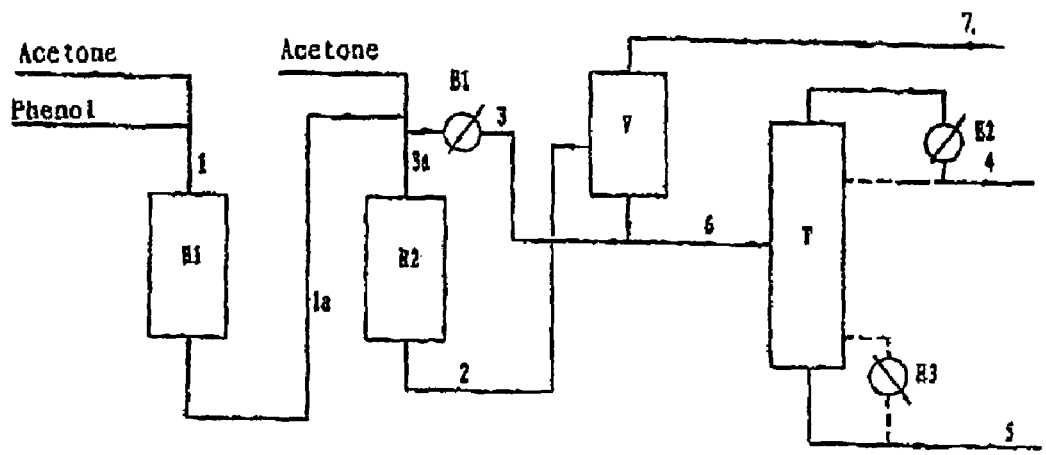
FIG. 3 is a schematic process flow diagram of another embodiment of the method according to the present invention for preparing bisphenol A.

In the present invention, said reaction zone is an adiabatic fixed bed reactor, or two or more adiabatic fixed bed reactors arranged in series, and said rectification zone can be a rectification column with side draws, a combination of a flash drum and a rectification column, or other devices and processes capable of removing lights and water (cf. FIG. 2 and FIG. 3). When said reaction zone comprises two or more adiabatic fixed bed reactors arranged in series, the dewatered cycled stream 3 (cf. FIG. 1) can be transferred into any one of the reactors, or into each reactor proportionally, and a heat exchanger (not shown) is provided at the inlet of each reactor to control the condensation temperature, and the stream from reaction may pass through an adsorption column to remove harmful impurities as desired practically.

In the first embodiment according to the present invention, said reaction zone includes two adiabatic fixed bed reactors arranged in series, said rectification zone is rectification column T (cf. FIG. 2), wherein water-depleted fraction 3 primarily containing phenol, bisphenol A and acetone, which is withdrawn via a side draw from said rectification column, is transferred into the last reactor, i.e. reactor R2, wherein a heat exchanger (not shown) is provided at the inlet of each reactor to control the reaction temperature.

In another embodiment according to the present invention, said reaction zone comprises two adiabatic fixed bed reactors arranged in series, said rectification zone comprises flash drum V and rectification column T (cf. FIG. 3), wherein part of water-depleted fraction 3 primarily containing phenol, bisphenol A and acetone, which is discharged from the bottom of flash drum V, is transferred into the last reactor, i.e. reactor R2, wherein a heat exchanger (not shown) is provided at the inlet of each reactor to control the reaction temperature, while the residual part of said water-depleted fraction 3 is transferred into rectification column T for further concentration.

EXAMPLES

The catalysts used in the following examples are Purolite CT-124 cation exchange resin (ex Purolite International Ltd.).

The conversion of acetone and selectivity of reaction are separately calculated as follows:

Conversion of acetone =(molar flow rate of fed acetone−molar flow rate of discharged acetone)/molar flow rate of fed acetone*100%

Selectivity of reaction=(molar flow rate of discharged bisphenol A−molar flow rate of fed bisphenol A)/molar flow rate of fed acetone*100%

Example 1

According to the process flow diagram as shown in FIG. 2, phenol and acetone were charged into reactor R1 which was charged with condensation catalyst. The stream 1a from reaction was cooled, and then mixed with a cycled stream from rectification column T and fresh acetone stream to obtain a reaction mixture stream 3a. The reaction mixture stream 3a was transferred into reactor R2, and the stream 2 from reaction was transferred into rectification column T. Water-depleted fraction 3 primarily containing phenol, bisphenol A and acetone was withdrawn via a side draw in liquid, cooled by heat exchanger E1, and transferred into reactor R2 as a cycled stream; the top fraction of the column was cooled by heat exchanger E2 and refluxed to obtain fraction 4 containing water, unreacted acetone and part of unreacted phenol; a bottom reboiling system was formed by heat exchanger E3. Product fraction 5 primarily containing bisphenol A and phenol was obtained at the bottom of the column, and said product fraction 5 was transferred into the crystallization zone to be further processed to obtain a bisphenol A product.

Both two reactors were fixed bed reactors with same structure and size and charged with same catalyst. Their inside diameters were 200 mm, and the catalyst beds were 400 mm in height.

The rectification column had an inside diameter of 200 mm, and charged with 3 sections of θ net ring packings, wherein a packed section above the feeding site was of 2 m in height and equivalent to 4 theoretical trays, the first packed section below the feeding site was of 1 m in height and equivalent to 2 theoretical trays, and the second packed section below the feeding site was of 2 m in height and equivalent to 4 theoretical trays.

The operation conditions of reactors R1, R2 and rectification column T were as follows:

For R1 and R2, the feed temperature was of 65° C., and the operation pressure was of 6 kg/cm² (gage pressure). The flow rate of the fed phenol was 3.7 kg/hr, and was totally fed into the first reactor R1. The flow rate of the fed acetone was 0.15 kg/hr to the first reactor R1, and was 0.15 kg/hr to the second reactor R2. The discharged stream from the first reactor was cooled to 65° C. The operation pressure of the rectification column was 100 mmHg (absolute pressure). The flow rate of the side draw was 40 kg/hr. The temperature rise in R2 was controlled within 6° C.

The compositions of each stream of reactors R1 and R2 and rectification column T were shown in Table 1 (based on weight percentage).

TABLE 1

| Stream | Phenol (wt %) | Water (wt %) | Acetone (wt %) | BPA (wt %) | 2,4-BPA (wt %) | Others (wt %) |
|---|---|---|---|---|---|---|
| Stream 1 into R1 | 96.1 | 0 | 3.9 | 0 | 0 | 0 |
| Stream 1a out of R1 | 85.18 | 1.00 | 0.7 | 12.4 | 0.30 | 0.42 |
| Stream 3a into R2 | 75.25 | 0.20 | 0.40 | 22.60 | 0.50 | 1.05 |
| Stream 2 out of R2 | 73.87 | 0.30 | 0.03 | 24.10 | 0.60 | 1.10 |
| top stream 4 out of T | 44.70 | 54.40 | 0.90 | 0 | 0 | 0 |
| side stream 3 out of T | 73.98 | 0.09 | 0.03 | 24.2 | 0.6 | 1.10 |
| bottom stream 5 out of T | 68.09 | 0 | 0 | 29.89 | 0.71 | 1.23 |

In the first reactor R1, the conversion of acetone was 83.5%, and the selectivity of reaction was 92%; and in the second reactor R2, the conversion of acetone was 86%, and the selectivity of reaction was 95.5%.

Comparative Example 1

Operations and conditions were identical to those in Example 1, except that part of the stream 2 out of reactor R2 was not dewatered, but cooled directly and cycled into reactor R2 in a cycled flow rate of 40 kg/hr; and residual part of stream 2 was transferred into the rectification column, wherein no side draw is withdrawn from the rectification column. The compositions of each stream were shown in Table 2 (based on weight percentage).

TABLE 2

| Stream | Phenol (wt %) | Water (wt %) | Acetone (wt %) | BPA (wt %) | 2,4-BPA (wt %) | Others (wt %) |
|---|---|---|---|---|---|---|
| stream 1 into R1 | 84.30 | 1.09 | 0.39 | 13.46 | 0.32 | 0.44 |
| stream 1a out of R1 | 83.18 | 1.19 | 0.05 | 14.76 | 0.35 | 0.47 |
| stream 3a into R2 | 73.92 | 2.20 | 0.40 | 21.98 | 0.50 | 1.00 |
| stream 2 out of R2 | 73.05 | 2.30 | 0.07 | 22.95 | 0.58 | 1.05 |
| top stream 4 out of T | 44.20 | 54.40 | 1.60 | 0 | 0 | 0 |
| bottom stream 5 out of T | 68.45 | 0 | 0 | 29.70 | 0.72 | 1.25 |

In the first reactor R1, the conversion of acetone was 83.5%, and the selectivity of reaction was 92%; and in the second reactor R2, the conversion of acetone was 81%, and the selectivity of reaction was 90%;

By comparison, after dewatered, the water content in the reaction stream entering into reactor R2 was reduced from 2.20% to 0.20%, and both the selectivity of reaction and the conversion of acetone were improved significantly.

Example 2

One fixed bed reactor was used, i.e. acetone, phenol and the cycled side stream from the rectification column were mixed to form a reaction mixture 3a, which directly entered into reactor R2. Except for above difference, all the other operations were identical to those in Example 1.

In the rectification column, no packing was above the feeding site, the first packed section below and adjacent to the feeding site was of 2 m in height and equivalent to 4 theoretical trays; and the second packed section below and from the feeding site was of 1 m in height and equivalent to 2 theoretical trays.

The operation conditions of reactor R2 and rectification column T were as follows:

For reactor R2, the flow rate of the fed phenol was of 3.7 kg/hr, the flow rate of the fed acetone was of 0.3 kg/hr, the feed temperature was of 75° C., and the operation pressure was of 4 kg/cm² (gage pressure). The operation pressure of rectification column T was 130 mmHg (absolute pressure), and no reflux was provided with said rectification column.

The location of side draw was between the two packed sections, and the cycled side flow rate was 24 kg/hr. The reaction temperature rise was controlled within 10° C.

The compositions of each stream of reactor R2 and rectification column T were shown in Table 3 (based on weight percentage).

TABLE 3

| Stream | Phenol (wt %) | Water (wt %) | Acetone (wt %) | BPA (wt %) | 2,4-BPA (wt %) | Others (wt %) |
|---|---|---|---|---|---|---|
| stream 3a into R2 | 76.90 | 0.97 | 0.56 | 20.85 | 0.30 | 0.42 |
| stream 2 out of R2 | 72.20 | 1.11 | 0.09 | 24.25 | 0.56 | 0.99 |
| top stream 4 out of T | 62.56 | 37.14 | 0.30 | 0 | 0 | 0 |
| side stream 3 out of T | 74.04 | 0.089 | 0.08 | 24.30 | 0.54 | 0.95 |
| bottom stream 5 out of T | 67.50 | 0 | 0 | 30.58 | 0.70 | 1.22 |

In reactor R2, the conversion of acetone was 87%, and the selectivity of reaction was 94%.

Comparative Example 2

Comparative Example 2 was substantially identical to Example 2, except that the cycled stream into reactor R2 was not dewatered, but cooled directly and cycled thereinto in a cycled flow rate of 24 kg/hr; no side draw is provided with the rectification column, and the discharged of the reactor was dewatered. The compositions of each stream were shown in Table 4 (based on weight percentage).

TABLE 4

| Stream | Phenol (wt %) | Water (wt %) | Acetone (wt %) | BPA (wt %) | 2,4-BPA (wt %) | Others (wt %) |
|---|---|---|---|---|---|---|
| stream 3a into R2 | 76.03 | 2.15 | 0.57 | 20.55 | 0.29 | 0.41 |
| stream 2 out of R2 | 74.27 | 2.29 | 0.11 | 21.81 | 0.55 | 0.97 |
| top stream 4 out of T | 43.68 | 53.80 | 2.52 | 0 | 0 | 0 |
| bottom stream 5 out of T | 68.45 | 0 | 0 | 29.59 | 0.71 | 1.25 |

In reactor R2, the conversion of acetone was 85%, and the selectivity of reaction was 91%;

By comparison, after dewatered, the water content in the reaction stream entering into reactor R2 was reduced from 2.15% to 0.97%, and both the selectivity of reaction and the conversion of acetone were improved significantly.

Example 3

Example 3 was substantially identical to Example 2, except that rectification column T was a three-sections packed column, wherein one packed section was above the feeding site, which was of 3 m in height and equivalent to 6 theoretical trays; the first packed section below and adjacent to the feeding site was of 3 m in height and equivalent to 6 theoretical trays; and the second packed section below and adjacent to the feeding site was of 4 m in height and equivalent to 8 theoretical trays.

The operation conditions of reactor R2 and rectification column T were as follows:

For reactor R2, the flow rate of the fed phenol was of 6 kg/hr, the flow rate of the fed acetone was of 0.3 kg/hr, the feed temperature was of 75° C., and the operation pressure was of 5 kg/cm² (gage pressure). The operation pressure of rectification column T was 760 mmHg (absolute pressure), and the cycled side flow rate was 90 kg/hr. The reaction temperature rise was controlled within 4° C.

The compositions of each stream of reactor R2 and rectification column T were shown in Table 5 (based on weight percentage).

TABLE 5

| Stream | Phenol (wt %) | Water (wt %) | Acetone (wt %) | BPA (wt %) | 2,4-BPA (wt %) | Others (wt %) |
|---|---|---|---|---|---|---|
| stream 3a into R2 | 76.90 | 0.60 | 0.36 | 20.85 | 0.25 | 0.40 |
| stream 2 out of R2 | 72.20 | 0.80 | 0.06 | 24.00 | 0.37 | 0.85 |
| top stream 4 out of T | 87.56 | 12.15 | 0.29 | 0 | 0 | 0 |
| side stream 3 out of T | 74.49 | 0.069 | 0.07 | 24.10 | 0.39 | 0.86 |
| bottom stream 5 out of T | 68.23 | 0 | 0 | 30.00 | 0.65 | 1.12 |

In reactor R2, the conversion of acetone was 87%, and the selectivity of reaction was 96.5%.

Example 4

Example 4 was substantially identical to Example 2, except that rectification column T was a sieve-plate column with an inside diameter of 200 mm, 25 trays and a tray efficiency of 30%.

The operation conditions of reactor R2 and rectification column T were as follows:

The flow rates of fed phenol and acetone were identical to those in Example 2. The feed temperature was 70° C., and the operation pressure was 5 kg/cm² (gage pressure). The operation pressure of rectification column T was 60 mmHg (absolute pressure), the feeding site was at the 6$^{th}$ tray, the side draw was at the 13$^{th}$ tray, and the cycled flow rate was 40 kg/hr. The reaction temperature rise was controlled within 6° C.

The compositions of each stream of reactor R2 and rectification column T were shown in Table 6 (based on weight percentage).

TABLE 6

| Stream | Phenol (wt %) | Water (wt %) | Acetone (wt %) | BPA (wt %) | 2,4-BPA (wt %) | Others (wt %) |
|---|---|---|---|---|---|---|
| stream 3a into R2 | 75.19 | 0.80 | 0.46 | 22.85 | 0.29 | 0.41 |
| stream 2 out of R2 | 72.98 | 1.09 | 0.08 | 24.35 | 0.53 | 0.97 |
| top stream 4 out of T | 62.18 | 37.54 | 0.28 | 0 | 0 | 0 |
| side stream 3 out of T | 73.96 | 0.078 | 0.07 | 24.37 | 0.54 | 0.98 |
| bottom stream 5 out of T | 67.83 | 0 | 0 | 30.28 | 0.68 | 1.21 |

The conversion of acetone was 87.5%, and the selectivity of reaction was 95%.

Example 5

According to the process flow diagram as shown in FIG. 3, phenol and acetone were charged into reactor R1, which was charged with condensation catalyst. Stream 1a from reaction was cooled, and then mixed with the cycled stream from the flash drum and fresh acetone stream to obtain reaction mixture stream 3a. The reaction mixture stream 3a was transferred into condensation reactor R2, and the stream 2 from reaction was transferred into flash drum V. Fraction 7 obtained at the top of the flash drum was recovered; part of the bottom stream of the flash drum was cycled into reactor R2 as water-depleted fraction 3, and the residual part was transferred to rectification column T as feed 6. The top fraction 4 of said rectification column T was recovered, while product fraction 5 primarily containing bisphenol A and phenol was obtained at the bottom of said rectification column T. Said product fraction 5 was transferred into the crystallization zone to be further processed to obtain a bisphenol A product.

The reactors were with the same structure and size as that in Example 1. The flash drum had an inside diameter of 300 mm, and a height of 600 mm. The rectification column had an inside diameter of 200 mm, and charged with two sections of θ net-ring packings, wherein the first packed section from the top of the column was of 2 m in height and equivalent to 4 theoretical trays, and the second packed section was of 2 m in height and equivalent to 4 theoretical trays. The feeding site was above the first packed section.

The operation conditions of reactors R1, R2 and rectification column T were as follows:

For R1 and R2, the feed temperature was of 73° C., and the operation pressure was of 4 kg/cm² (gage pressure). The flow rate of the fed phenol was 4.5 kg/hr, and was totally added into the first reactor R1. The flow rate of the fed acetone was 0.21 kg/hr to the first reactor R1, and was 0.09 kg/hr to the second reactor R2. The flash drum had an operation pressure of 50 mmHg (absolute pressure), and a cycled flow rate of 40 kg/hr (stream 3). The operation pressure of the rectification column was 50 mmHg (absolute pressure).

The compositions of each stream of reactors R1 and R2 and rectification column T were shown in Table 7 (based on weight percentage).

TABLE 7

| Stream | Phenol (wt %) | Water (wt %) | Acetone (wt %) | BPA (wt %) | 2,4-BPA (wt %) | Others (wt %) |
|---|---|---|---|---|---|---|
| stream 1 into R1 | 93.75 | 0 | 6.25 | 0 | 0 | 0 |
| stream 1a out of R1 | 81.68 | 1.32 | 0.60 | 15.40 | 0.42 | 0.58 |
| stream 3a into R2 | 74.35 | 0.88 | 0.49 | 22.96 | 0.44 | 0.88 |
| stream 2 out of R2 | 73.60 | 0.96 | 0.26 | 23.84 | 0.45 | 0.89 |
| cycled stream 3 out of V | 73.63 | 0.83 | 0.25 | 23.94 | 0.45 | 0.90 |
| feed stream 6 into T | 73.63 | 0.83 | 0.25 | 23.94 | 0.45 | 0.90 |
| Top stream 7 out of V | 67.67 | 28.83 | 3.41 | 0 | 0 | 0 |
| top stream 4 out of T | 94.57 | 4.12 | 1.23 | 0 | 0 | 0 |
| bottom stream 5 out of T | 68.33 | 0 | 0 | 30.00 | 0.56 | 1.11 |

In the first reactor R1, the conversion of acetone was 83.5%, and the selectivity of reaction was 92%; in the second reactor R2, the conversion of acetone was 88%, and the selectivity of reaction was 96%. This example indicates that a combination of a flash drum and a rectification column is capable of bringing out the substantial same effects as a rectification with side draws.

Crystallization Examples

As to the product fractions primarily containing bisphenol A and phenol obtained in Examples 1 to 5 and Comparative Examples 1 to 2, an adduct crystal of bisphenol A and phenol was obtained by carrying out the crystallization once only. The crystal slurry was filtered, and the filter cake was washed with pure phenol, then the residual phenol was removed to obtain a bisphenol A product, wherein the crystallization temperature was 45° C., and weight of the phenol used for washing the filter cake was 0.5 times as that of the filter cake. The compositions of the obtained products were shown in Table 8.

TABLE 8

| Example | BPA (wt %) | Phenol (ppm) | Color APHA | 2,4-BPA (ppm) | Ashes (ppm) | Iron (ppm) |
|---|---|---|---|---|---|---|
| Example 1 | 99.91 | 20 | 15 | 190 | 14 | <0.1 |
| Comparative Example 1 | 99.90 | 20 | 18 | 190 | 14 | <0.1 |
| Example 2 | 99.92 | 18 | 12 | 185 | 13 | <0.1 |
| Comparative Example 2 | 99.90 | 20 | 20 | 190 | 14 | <0.1 |
| Example 3 | 99.93 | 10 | 5 | 150 | 5 | <0.1 |

TABLE 8-continued

| Example | BPA (wt %) | Phenol (ppm) | Color APHA | 2,4-BPA (ppm) | Ashes (ppm) | Iron (ppm) |
|---|---|---|---|---|---|---|
| Example 4 | 99.93 | 12 | 10 | 170 | 10 | <0.1 |
| Example 5 | 99.93 | 15 | 10 | 150 | 10 | <0.1 |

According to the data shown in Table 8, after once crystallization only, from the product fractions primarily containing bisphenol A and phenol according to the method of the present invention can obtain the bisphenol A products, which meet the specification completely.

What is claimed is:

1. A method for preparing bisphenol A, comprising the following steps:
    transferring phenol and acetone into a reaction zone charged with condensation catalyst, obtaining a stream containing bisphenol A after reaction;
    transferring the obtained stream containing bisphenol A into a rectification zone obtaining a product fraction primarily containing bisphenol A and phenol; and
    transferring the product fraction primarily containing bisphenol A and phenol into a crystallization zone to obtain a bisphenol A product;
    wherein said rectification zone is a rectification column, and a water-depleted fraction in liquid primarily containing phenol, bisphenol A, and acetone and having a water content that is controlled at a level of not greater than 2% by weight is obtained as a side draw from the rectification column, and wherein said water-depleted fraction is cooled and returned as a cycled stream to the reaction zone.

2. The method according to claim 1, wherein said reaction zone is an adiabatic fixed bed reactor comprising one adiabatic fixed bed reactor or two or more adiabatic fixed bed reactors arranged in series.

3. The method according to claim 2, wherein when said reaction zone comprises two or more adiabatic fixed bed reactors arranged in series, the water-depleted fraction primarily containing phenol, bisphenol A and acetone is returned to any one of the reactors or to each reactor proportionally.

4. The method according to claim 3, wherein when said reaction zone comprises two or more adiabatic fixed bed reactors arranged in series, the water-depleted fraction primarily containing phenol, bisphenol A and acetone is returned to the last reactor only.

5. The method according to claim 3, wherein the weight ratio of the cycled flow rate of said water-depleted fraction primarily containing phenol, bisphenol A and acetone to the flow rate of the feed stream to the reactor, into which said water-depleted fraction enters, is in the range from 5:1 to 15:1.

6. The method according to claim 4, wherein the weight ratio of the cycled flow rate of said water-depleted fraction primarily containing phenol, bisphenol A and acetone to the flow rate of the feed stream to the reactor, into which said water-depleted fraction enters, is in the range from 5:1 to 15:1.

7. The method according to claim 1, wherein the product fraction primarily containing bisphenol A and phenol is discharged from the bottom of said rectification column.

8. The method according to claim 1, wherein the operation pressure of said rectification column is in the range of 50-800 mmHg absolute pressure.

9. The method according to claim 1, wherein the molar ratio of phenol to acetone in said reaction zone is in the range from 3:1 to 30:1, the condensation temperature in said reaction zone is in the range of 50-130° C., and the condensation pressure is from atmosphere to 6 kg/cm$^2$ gage pressure.

10. The method according to claim 4, wherein the molar ratio of phenol to acetone in said reaction zone is in the range from 3:1 to 30:1, the condensation temperature in said reaction zone is in the range of 50-130° C., and the condensation pressure is from atmosphere to 6 kg/cm$^2$ gage pressure.

11. The method according to claim 1, wherein in the crystallization zone the crystallization is carried out once only.

12. The method according to claim 4, wherein in the crystallization zone the crystallization is carried out once only.

* * * * *